United States Patent [19]

Hishida

[11] Patent Number: 4,810,349
[45] Date of Patent: Mar. 7, 1989

[54] OXYGEN CONCENTRATION SENSOR WITH AN IMPROVED ELECTRICAL CONNECTION FOR THE TRANSMISSION OF DIFFERENT OPERATING VOLTAGES

[75] Inventor: Hiroaki Hishida, Saitama, Japan

[73] Assignee: Honda Giken Kogyo Kabushiki Kaisha, Tokyo, Japan

[21] Appl. No.: 910,920

[22] Filed: Sep. 24, 1986

[30] Foreign Application Priority Data

Sep. 28, 1985 [JP] Japan .......................... 60-148880[U]

[51] Int. Cl.$^4$ ............................................ G01N 27/46
[52] U.S. Cl. .................................... 204/406; 204/412; 204/425
[58] Field of Search ............... 204/406, 425, 431, 424, 204/427, 412, 1 T; 429/130, 623, 624, 626; 123/440, 489

[56] References Cited

U.S. PATENT DOCUMENTS

| | | | |
|---|---|---|---|
| 4,505,807 | 3/1985 | Yamada | 204/425 |
| 4,591,421 | 5/1986 | Yamada et al. | 204/406 |
| 4,601,809 | 7/1986 | Kitahara | 204/406 |
| 4,624,770 | 11/1986 | Yamada | 204/425 |
| 4,629,549 | 12/1986 | Kojima et al. | 204/406 |
| 4,642,174 | 2/1987 | Shibata | 204/425 |
| 4,658,790 | 4/1987 | Kitahara | 204/425 |

FOREIGN PATENT DOCUMENTS 60-120354 8/1985 Japan .

Primary Examiner—John F. Niebling
Assistant Examiner—Ben C. Hsing
Attorney, Agent, or Firm—Pollock, VandeSande & Priddy

[57] ABSTRACT

An oxygen concentration sensor for electrically sensing oxygen concentration in a gaseous body, including an oxygen pump element, a sensor cell element whose operating voltage is relatively low, and a heater element for heating the sensor cell element. For the electrical connection, the oxygen concentration sensor is provided with a first connector having terminals connected to the oxygen pump element and the heater element whose operating voltages are relatively high, and a second connector discretely from the first connector and having only terminals connected to the sensor cell element so that leakage of the relatively high operating voltage to the terminals of the sensor cell element is prevented.

2 Claims, 3 Drawing Sheets

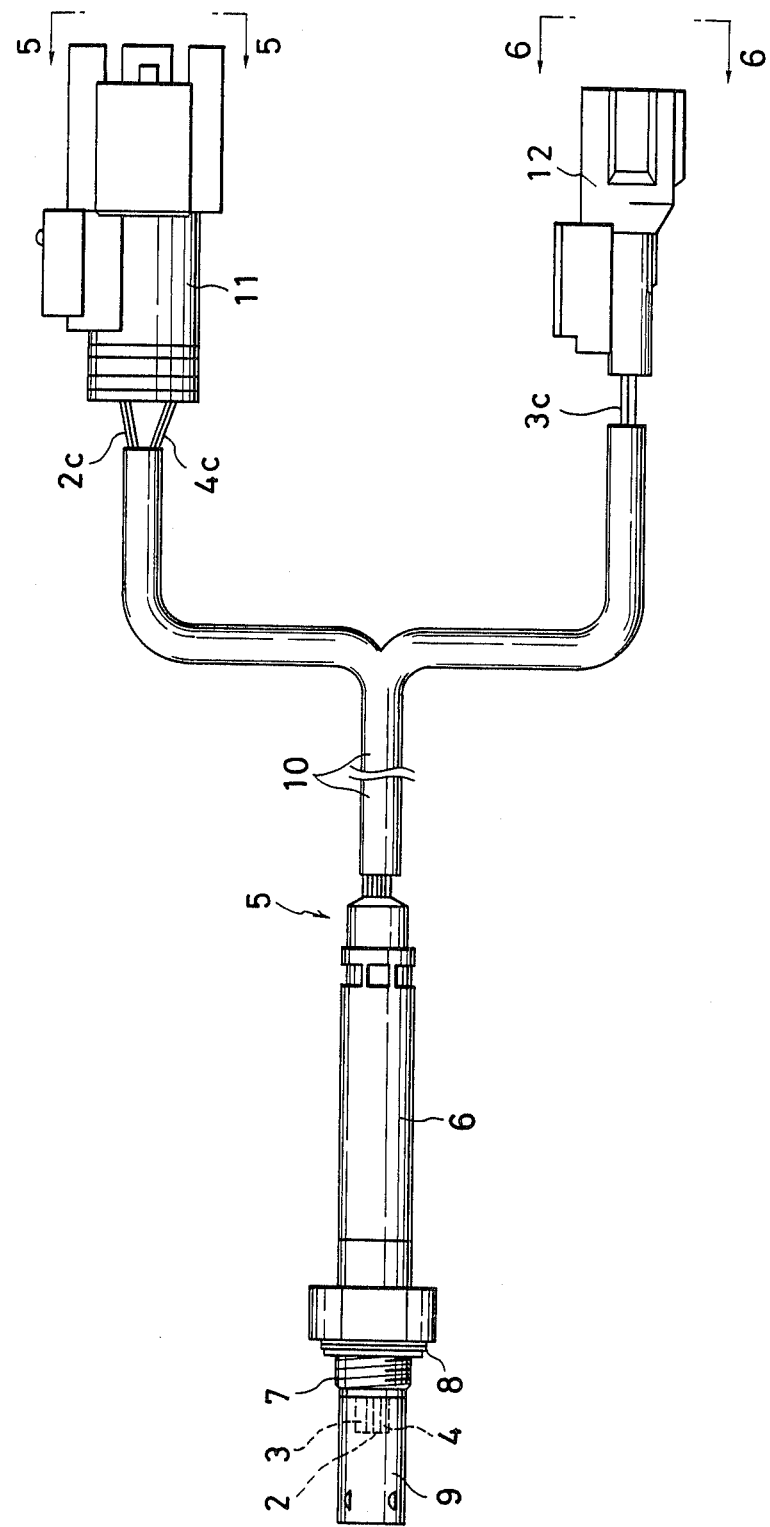

OXYGEN CONCENTRATION SENSOR WITH AN IMPROVED ELECTRICAL CONNECTION FOR THE TRANSMISSION OF DIFFERENT OPERATING VOLTAGES

BACKGROUND OF THE INVENTION

1. Field of the Invention

The present invention relates to an oxygen concentration sensor, and more particularly to an oxygen concentration sensor with an electrical connection suited for the transmission of different operating voltages.

2. Description of Background Information

Feedback control of the air/fuel ratio is generally utilized for controlling an internal combustion engine for the purification of exhaust gas and improvements of the fuel economy. For such a feedback control, oxygen concentration in exhaust gas is detected and the air/fuel ratio of mixture to be supplied to the engine is controlled in response to a result of detection.

Recently, a type of oxygen concentration sensor has been developed which can generate an output signal whose level is proportional to the oxygen concentration in exhaust gas. With such an oxygen concentration sensor, air/fuel ratio of the mixture to be taken into the engine is controlled very minutely.

For example, Japanese Patent Application Laid Open No. 58-153155 discloses an oxygen concentration sensor disposed in the exhaust gas of an internal combustion engine, which comprises an oxygen pump element (referred to simply as "pump element" hereinafter) an oxygen concentration detection cell element (referred to as "cell element" hereinafter), both made of an oxygen-ion conductive solid electrolyte member and a heater element for heating up the pump element and the cell element in proportion to an electric power current supplied thereto. By this measure, the pump element and the cell element are activated and the oxygen concentration in the exhaust gas is electrically sensed by means of these elements (also referred to as sensor elements) cooperating with each other. This type of oxygen concentration sensor is connected to a control unit for a feedback control of the air/fuel ratio of intake mixture on the basis of an output signal of the oxygen concentration sensor, and for maintaining a desirable operating condition of the oxygen concentration sensor.

FIGS. 1-3 show an example of the oxygen concentration sensor which is to be connected to a control unit for a sensing operation. As shown, the connection is performed by means of a single connector 1 having a plurality of terminals therein. More particularly, the oxygen concentration sensor shown in these figures includes a pump element 2', a cell element 3' and a heater element 4'. The connector 1 includes terminals 2a' and 2b' for the pump element 2', terminals 3a' and 3b' for the cell element 3', and terminals 4a' and 4b' for a heater element 4' which are arranged parallel to each other.

Through the terminals 3a' and 3b', a relatively low operating voltage of, for example 0 through 80 mV, from the cell element 3' is transmitted. On the other hand, through the terminals 2a' and 2b', 4a' and 4b', relatively high operating voltages of the pump element 2' and the heater element 4', for example 0 through 14 V, are transmitted. Therefore, in the event that water permeates into the inside of connector 1, leakage of the relatively high voltage of the pump element 2' and the heater element 4' into the terminals 3a' and 3b' may occur. If such a leakage occurs, it may result in an abnormal state of the output signal of the oxygen concentration sensor or damage to electric circuits in the control unit.

OBJECT AND SUMMARY OF THE INVENTION

An object of the present invention is therefore to provide an oxygen concentration detection device which is free from the leaking of the current of relatively high voltage level into terminals connected to the cell element whose operating voltage is relatively low.

According to the present invention, the oxygen concentration sensor comprises discrete connectors for groups of signals to or from sensor elements whose operating voltages are different among groups.

Further scope and applicability of the present invention will become apparent from the detailed description given hereinafter. However, it should be understood that the detailed description and specific example, while indicating a preferred embodiment of the invention, are given by way of illustration only, since various changes and modifications within the spirit and scope of the invention will become apparent to those skilled in the art from this detailed description.

BRIEF DESCRIPTION OF THE DRAWINGS

FIG. 4 is a side view in elevation of a preferred embodiment of the oxygen concentration sensor according to the present invention;

DETAILED DESCRIPTION OF A PREFERRED EMBODIMENT

Figure 5:
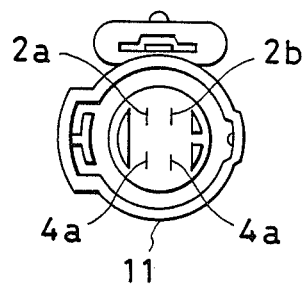
FIG. 5 is an end view in elevation of the oxygen concentration sensor taken along the lines 5—5 of FIG. 4, showing the arrangement of terminals in one of the connectors.
Figure 6:
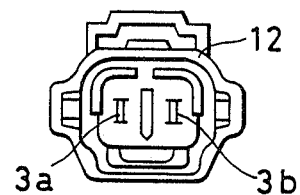
FIG. 6 is an end view in elevation of the oxygen concentration sensor taken along the lines 6—6 of FIG. 4, showing the arrangement of terminals in another one of the connectors.

The preferred embodiment of the present invention will be described hereinafter with reference to FIGS. 4-6 of the accompanying drawings.

Figure 1:
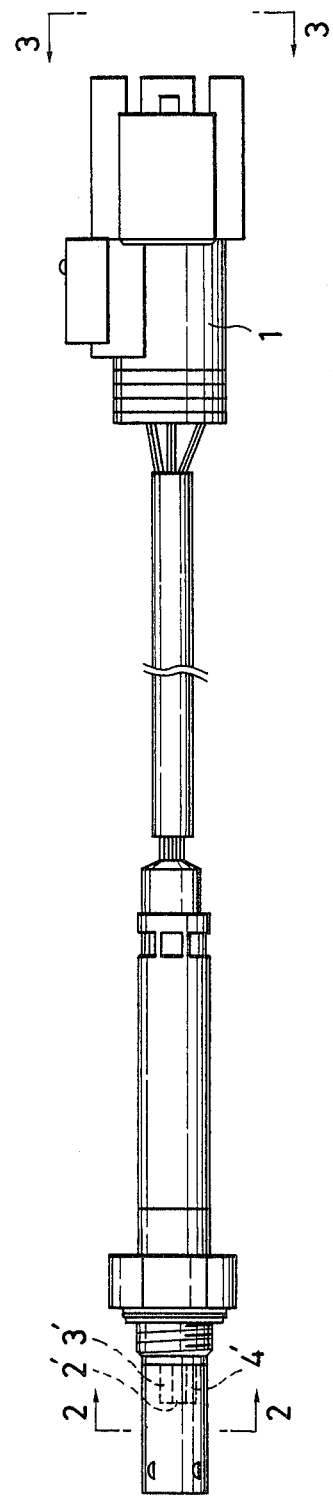
FIG. 1 is a side view in elevation of a conventional oxygen concentration sensor which has a single connector.
Figure 3:
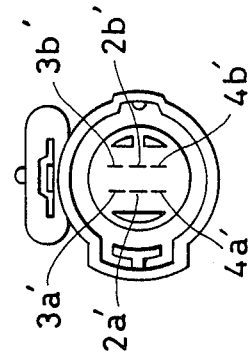
FIG. 3 is an end view in elevation of the oxygen concentration sensor showing the structure of the connector, taken along the line 3—3 of FIG. 1.
Figure 2:
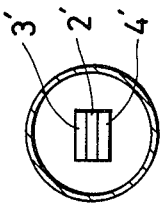
FIG. 2 is a cross-sectional view of the oxygen concentration sensor taken on the plane of lines 2—2 of FIG. 1 showing the arrangement of the sensor elements in a cylindrical cap.

As shown in FIG. 4, the oxygen concentration sensor according to the present invention which is generally denoted by 5 includes, as the conventional oxygen concentration sensor, an oxygen pump element 2 (pump element) and an oxygen concentration detection cell element 3 (cell element), both made of an oxygen-ion conductive solid electrolyte member, and a heater element 4 for heating the pump element 2 and the cell element 3. These elements 2 through 4 are fixed at an end portion of a housing member 6. Outer surface of this end portion of the housing member is threaded to form a thread portion 7 so that the housing member 6 is screwed via a gasket 8 on an exhaust manifold of an internal combustion engine. When the oxygen concentration sensor 5 is mounted on the exhaust manifold in this way, sensor elements, i.e. the pump element 2, the cell element 3, and the heater element 4, are disposed in the passage of exhaust gas. The sensor elements 2-4 are surrounded by a cylindrical cap 9 with gas introducing holes which operates as a protective cover and has a closed end. The cylindrical cap 9 is fitted into the end of the housing member 6 at the circumference of an open end thereof. The operating voltages of the sensor elements 2-4 are, as explained with reference to FIG. 1, 0 through 80 mV for the cell element 3, and 0 through 14 V for the pump element 2 and the heater element 4.

Lead wires 2c through 4c for transmitting signals to and from the sensor elements 2 through 4 are provided and respectively covered by a covering material such as "Teflon". The lead wires 2c through 4c are further protected by a heat insulating protection tube 10 outside the housing member 6. Two connectors, i.e. a first connector 11 having terminals 2a and 2b, 4a and 4b, and a second connector 12 having terminals 3a and 3b, are provided for the electrical connection of the oxygen concentration sensor 5. As illustrated, the protection tube 10 is branched off near its ends on the opposite side of the housing member 6.

Lead wires 2c and 4c from the pump element 2 and the heater element 4 whose operating voltages are relatively high are connected to terminals 2a and 2b, 4a and 4b in the first connector 11. On the other hand, the lead wire 3c from the cell element 3 whose operating voltage is relatively low is connected to the terminals 3a and 3b in the second connector 12. These first and second connectors 11 and 12 can be readily connected to a control unit (disposed at a suitable position of a vehicle body on which the internal combustion engine is mounted, however not illustrated in the figure) for a feedback control of the air/fuel ratio of mixture to be sucked into the engine. The first connector 11 and the second connector 12 themselves are preferably made watertight when connected, so as to prevent permeation of water which may cause a failure of the oxygen concentration sensor 5.

Thus, according to the present invention, the oxygen concentration sensor is provided with discrete connectors for transmitting groups of signals to or from the sensor elements whose operating voltages are different among different groups. With this provision, it becomes possible to prevent the leakage of the voltage applied to the terminal for a sensor element having a high operating voltage into the terminals for a sensor element having a low operating voltage even if the permeation of water into the connector occurs. Thus, a very stable operation of the oxygen concentration sensor as compared with the conventional arrangement is enabled.

Further, due to this advantageous effect of the present invention, it is now unnecessary to provide a protection circuit in the control unit which was often adopted in conventional arrangement for protecting a circuit for treating signals from an element of relatively low operating voltage.

What is claimed is:

1. An oxygen concentration sensor to be electrically connected to a control unit for controlling an air/fuel ratio of mixture to be supplied to an internal combustion engine, comprising:
   an oxygen pump element made of an oxygen-ion conductive solid electrolyte;
   an oxygen concentration ratio sensing cell element also made of the oxygen-ion conductive solid electrolyte;
   a heater element for heating said oxygen concentration ratio sensing cell element;
   first and second connectors each having a plurality of terminals, for detachably connecting said terminals of said oxygen concentration sensor to corresponding terminals of said control unit electrically, wherein said first connector includes terminals which are respectively electrically connected to said oxygen pump element and said heater element, and said second connector includes only terminals which are electrically connected to said oxygen concentration ratio sensing cell element;
   a first set of lead wires which electrically connects said oxygen pump element and said heater element to said first connector; and
   a second set of lead wires which connects said oxygen concentration ratio sensing cell element to said second connector.

2. An oxygen concentration sensor as set forth in claim 1, wherein said oxygen concentration ratio sensing cell element generates an electromotive force which is much smaller than voltages to be applied to said oxygen pump element and said heater element.

* * * * *